United States Patent [19]
Viitala

[11] Patent Number: 4,643,713
[45] Date of Patent: Feb. 17, 1987

[54] VENOUS RESERVOIR

[75] Inventor: Daniel W. Viitala, Round Lake Beach, Ill.

[73] Assignee: Baxter Travenol Laboratories, Inc., Deerfield, Ill.

[21] Appl. No.: 667,985

[22] Filed: Nov. 5, 1984

[51] Int. Cl.$^4$ .............................................. A61M 5/00
[52] U.S. Cl. ...................................... 604/4; 604/122; 128/DIG. 3; 55/159
[58] Field of Search .................. 604/4, 122, 317, 124, 604/126, 408, 319; 128/DIG. 3; 55/159

[56] References Cited

U.S. PATENT DOCUMENTS

| | | | |
|---|---|---|---|
| 3,058,464 | 10/1962 | Broman | 128/DIG. 3 |
| 3,342,019 | 9/1967 | Smythe | 55/159 |
| 3,827,562 | 8/1974 | Esmond | 604/122 |
| 3,827,860 | 6/1974 | Burlis | 128/DIG. 3 |
| 3,849,071 | 11/1974 | Kayser | 128/DIG. 3 |
| 3,907,504 | 9/1975 | Hammond et al. | 128/DIG. 3 |
| 3,918,912 | 11/1975 | Taloon | 128/DIG. 3 |
| 4,428,743 | 1/1984 | Heck | 604/4 |
| 4,493,705 | 1/1985 | Gordon et al. | 604/4 |

FOREIGN PATENT DOCUMENTS 3328562 2/1984 Fed. Rep. of Germany .

Primary Examiner—C. Fred Rosenbaum
Assistant Examiner—Karen L. Kaechele
Attorney, Agent, or Firm—Paul C. Flattery; Kay H. Pierce

[57] ABSTRACT

A venous reservoir is provided in which a blood inlet (42) is located at an inlet end (70) of the container (48) which extends upwardly with a fast rise and for a sufficient distance to allow the blood entering the inlet to enter a large volume and to expand rapidly. The top (74) of the inlet end wall (70) of the container communicates with a vent outlet (46) whereby a sharp decrease in the velocity of the blood flow resulting from its rapid expansion provides buoyancy to air in the blood causing air bubbles to rise to the top of the container and be vented through the vent opening. A top wall (76) of the container extends from the vent opening and toward a blood outlet (44), with the top wall being curved in a manner to prevent the velocity of blood from increasing until the blood is substantially at the blood outlet. The top wall (76) includes a curved portion (80) opposite to the inlet end (70) whereby the air bubbles that have not been discharged immediately upon entering the reservoir may flow back up the top wall to the vent opening.

4 Claims, 2 Drawing Figures

VENOUS RESERVOIR

TECHNICAL FIELD

This invention concerns a blood treatment system including a novel venous reservoir.

BACKGROUND ART

During cardiopulmonary by-pass surgery wherein an oxygenator, venous reservoir and cardiotomy reservoir are conventionally used, it is extremely important that any air in the blood be vented so that air bubbles do not enter the oxygenator. Typically, blood from the cardiotomy reservoir and the patient flows into the venous reservoir inlet, and the blood is drawn by a venous pump from the venous reservoir and is pumped into the oxygenator. Between the outlet of the venous reservoir and the oxygenator, there is often a bubble detector to detect the presence of air bubbles in the blood flowing to the oxygenator, which air bubbles can cause a dangerous condition.

It is an object of the present invention to provide a venous reservoir in which the air carried by the blood entering the venous reservoir is thoroughly vented, in order to prevent air bubbles from exiting the venous reservoir and entering the downstream oxygenator.

Another object of the present invention is to provide a blood treatment system in which the lines to and from the venous reservoir are as short as possible, and in addition provide a venous reservoir in which there is effective air venting.

A further object of the present invention is to provide a blood treatment system which is relatively simple and efficient in operation.

Other objects and advantages of the present invention will become apparent as the description proceeds.

SUMMARY OF THE INVENTION

In accordance with the present invention, a venous reservoir is provided comprising a container having a venous blood inlet, a venous blood outlet and a vent outlet. The inlet is located at an inlet end of the container with the wall defining the inlet end extending upwardly with a fast rise and for a sufficient distance to allow the blood to enter a large volume and expand rapidly. The top of the inlet end wall communicates with the vent outlet whereby a sharp decrease in the velocity of the blood flow results from its rapid expansion. This provides buoyancy to air in the blood, causing air bubbles to rise to the top of the container and be vented through the vent opening.

In the illustrative embodiment, the inlet end lies within a plane that is at a sharp angle with respect to the inlet axis. A top wall extends from the vent opening and toward the outlet with the top wall being curved in a manner to prevent the velocity of the blood from increasing until the blood is substantially at the blood outlet. The top wall extends forwardly and downwardly with a curved portion opposite to the inlet. In this manner, air bubbles that have not been discharged immediately upon entering the reservoir may flow back up the top wall to the vent opening.

In the illustrative embodiment, the inlet is located at the bottom of the inlet wall and the vent opening is located at the top thereof. The vent opening and the inlet are spaced from each other as far as possible at the inlet end. The inlet is located in a horizontal plane that is higher than the horizontal plane in which the outlet is located, with the inlet axis being perpendicular to the outlet axis and with the vent opening axis being parallel to the outlet axis.

In the illustrative embodiment, a blood treatment system is provided which comprises a blood treatment device (e.g., an oxygenator) having a blood inlet, a blood outlet and a blood treatment medium (e.g., oxygen) inlet. The system also includes a venous reservoir having a blood inlet, an air vent and a blood outlet. The system further comprises a vented cardiotomy reservoir having a blood inlet and a blood outlet, and also includes a suction pump having a blood inlet and a blood outlet for pumping excess blood from the operating area and to the cardiotomy reservoir. Means are provided for connecting the blood outlet of the suction pump to the cardiotomy reservoir blood inlet. Means are provided for coupling the blood inlet of the suction pump to the operating area for receiving excess blood. Means are also provided for connecting the blood inlet of the suction pump to the venous reservoir air vent. Means are provided for connecting the cardiotomy reservoir blood outlet to the venous reservoir blood inlet. Means are provided for connecting the venous reservoir blood outlet to the blood inlet of the treatment device (e.g., the oxygenator). Means are provided for connecting the blood outlet of the blood treatment device to the venous reservoir blood inlet, and means are provided for connecting the blood outlet of the blood treatment device to the patient.

A more detailed explanation of the invention is provided in the following description and claims, and is illustrated in the accompanying drawings.

DETAILED DESCRIPTION OF THE ILLUSTRATIVE EMBODIMENT

Figure 1:
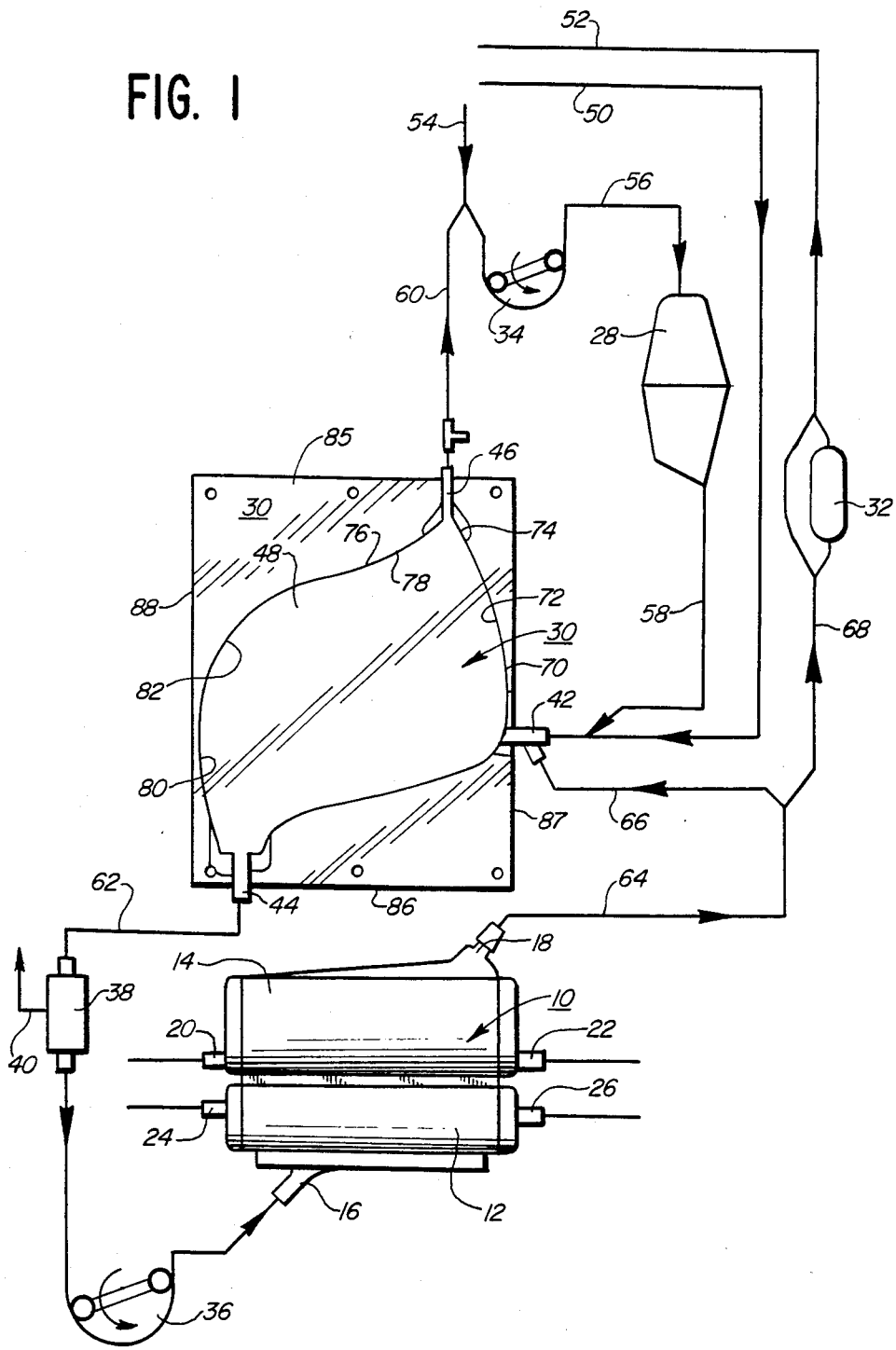
FIG. 1 is a schematic diagram of a blood treatment system constructed in accordance with the principles of the present invention.

Referring to FIG. 1, a blood treatment system in the form of a system for oxygenating the blood during cardiac surgery is illustrated therein. The system comprises a hollow fiber oxygenator 10 including a heat exchanger portion 12 and an oxygenation portion 14, a blood inlet 16, a blood outlet 18, an oxygen inlet or outlet 20, an oxygen inlet or outlet 22, a water inlet 24 and a water outlet 26. The system also includes a vented cardiotomy reservoir 28, a venous reservoir 30 to be described in more detail below, an arterial filter 32, a suction pump 34, a roller pump 36, and an ultrasonic bubble detector 38 having a monitoring line 40.

Venous reservoir 30 includes a blood inlet 42, a blood outlet 44, and a vent outlet 46. Inlet 42 and outlets 44 and 46 communicate with the venous reservoir bag 48 which has a unique and significant shape as is described in more detail below with reference to FIG. 2.

A first blood tube 50 from the patient's vena cava is connected directly to inlet 42 of venous reservoir 30. Blood is returned to the patient's aorta via tube 52. An intermediate blood suction line 54 is utilized for salvaging excess blood and is connected to the inlet of suction pump 34, the outlet of which is connected via line 56 to the inlet of cardiotomy reservoir 28. The outlet of cardiotomy reservoir 28 is connected via line 58 to inlet 42.

The air vent 46 of venous reservoir 30 is connected via line 60 to the inlet of suction pump 34. In this manner, the same vacuum source, suction pump 34, is used for both drawing excess blood from the operating area via line 54 and for drawing air via line 60 from venous reservoir 30.

Air-free blood from venous reservoir 30 flows from outlet 44, via line 62 and through ultrasonic bubble detector 38 and roller pump 36 to blood inlet 16 of oxygenator 10. The oxygenated blood flows via line 64 to inlet 42 via line 66 and to arterial filter 32 via line 68. Blood flowing through arterial filter 32 is then carried by tube 52 back to the patient's aorta.

Figure 2:
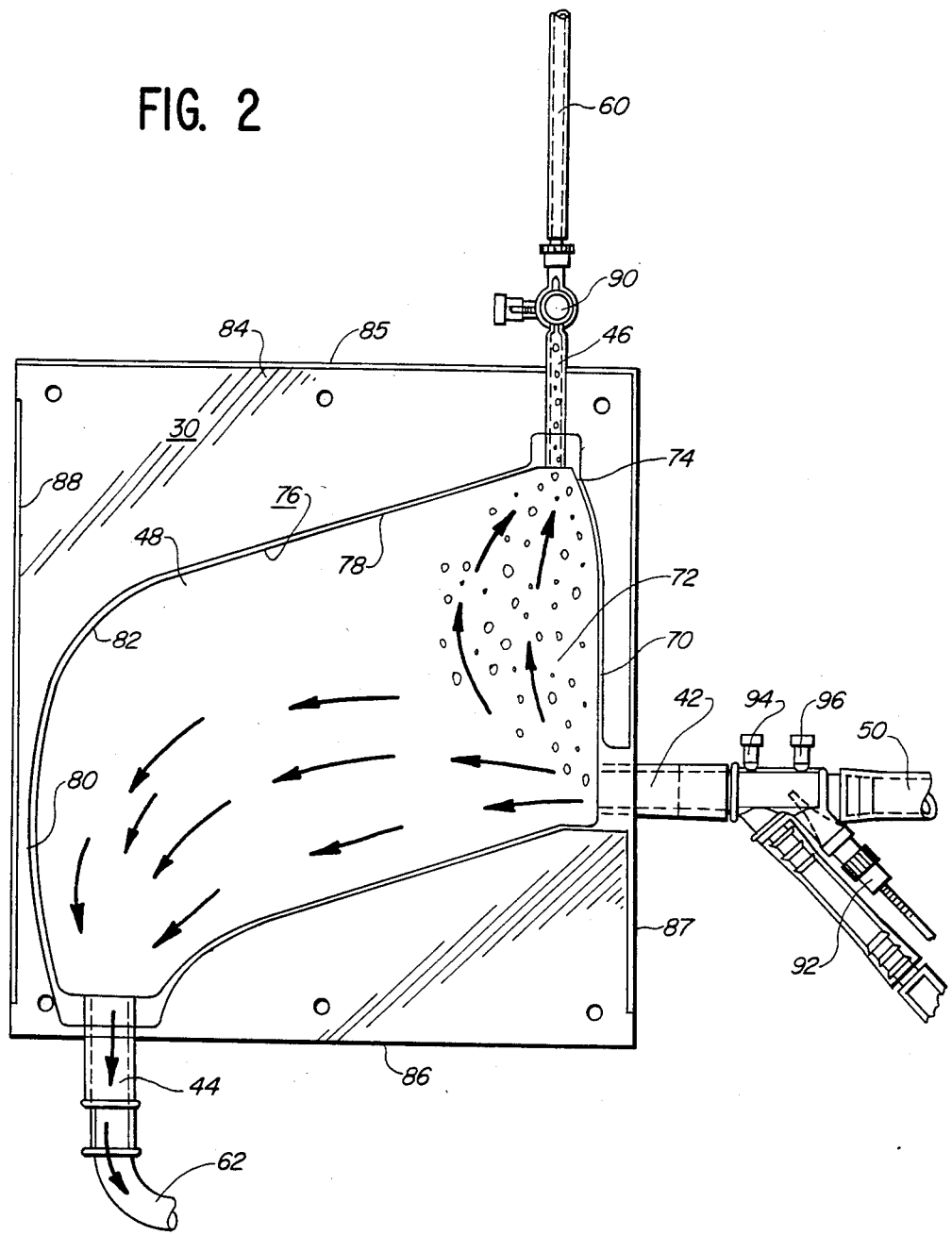
FIG. 2 is a side elevational view of a venous reservoir constructed in accordance with the principles of the present invention.

Referring now to FIG. 2, venous reservoir 30 is illustrated in more detail therein. It can be seen that inlet 42 is located at the inlet end 70 of container 48, with the wall 72 which defines the inlet end 70 extending upwardly with a fast rise and for a sufficient distance to allow the blood passing through inlet 42 to immediately enter a large volume and to expand rapidly. The inlet end lies in a plane that is at a sharp angle, approaching 90°, with respect to the axis of inlet 42. The top 74 of the inlet end wall 70 communicates with vent outlet 46. The aforesaid configuration provides a sharp decrease in the velocity of the blood entering inlet 42 resulting from its rapid expansion. This provides buoyancy to air in the blood, causing air bubbles to rise to the top of the container and be vented through vent opening 46.

Venous reservoir 30 comprises a top wall 76 extending from vent opening 46 and toward outlet 44. The top wall 76 extends forwardly with respect to portion 78 thereof and then downwardly with respect to portion 80 thereof, with a curved portion 82 opposite inlet 42. The configuration of top wall 78 is such as to prevent the velocity of the blood from increasing until the blood is substantially at the blood outlet 44. The configuration is such that the air bubbles that have not been discharged immediately upon entering the reservoir may flow back up the top wall 76 to the vent opening 46.

The inlet 42 is located at the bottom of inlet wall 72 and the vent opening 46 is located at the top therein. The vent opening 46 and inlet 42 are spaced as far from each other as possible at the inlet end 70. Likewise, the outlet 44 is diagonally spaced as far as possible from vent 46, and inlet 42 is located in a horizontal plane that is higher than the horizontal plane in which outlet 44 is located. The axis of inlet 42 is perpendicular to the axis of outlet 44 and the axis of vent opening 46 is parallel to the axis of outlet 44. By having outlet 44 at a lower level than inlet 42, good gravity drain is provided. Further, the perpendicular orientation of inlet 42 with respect to outlets 44 and 46 enable the lines to be kept as short as possible and also provide effective air venting.

The venous reservoir of the present invention may be formed of conventional medical container material, such as vinyl plastic, and may be formed in various sizes, such as one-half liter, one liter and two liters. In the illustrative embodiment, venous reservoir 30 is formed of two rectangular plastic sheets 84 which are sealed together but with the bag portion 48 being formed by the sheets 84. Sheets 84 are defined by top edges 85, bottom edges 86, and side edges 87 and 88. In order for different sizes of the venous reservoirs to be utilized with the same oxygenation apparatus, it is preferred that the distance between sides 87 and 88 be constant, notwithstanding the different sizes of reservoir volume.

In the illustrative embodiment of FIG. 2, air vent 46 is connected to a three-way stopcock 90 and a venous temperature monitor probe 92 is coupled to inlet 42. Also coupled to inlet 42 is a medicament injection site 94 and an injection site 96 for retrieving a venous sample.

Although no limitation is intended, in the illustrative embodiment, venous reservoirs having volumes of one-half liter, one liter and two liters had a dimension from side edge 87 to side edge 88 of 9.5 inches. In the one-half liter construction, the distance from top edge 85 to bottom edge 86 is $8\frac{3}{8}$ inches; in the one liter construction the distance from top edge 85 to bottom edge 86 is $10\frac{1}{4}$ inches; and in the two liter construction the distance from top edge 85 to bottom edge 86 is $12\frac{3}{8}$ inches. The axis of inlet 42 is perpendicular to side 87 and wall 72 of the container extends upwardly perpendicular to the axis of inlet 42 with a slight bend before vent 46. Top portion 78 extends leftwardly and downwardly (with respect to FIG. 2) at an angle of about 15° to 20°, preferably about 17° with respect to the horizontal, while curved wall 82 couples top portion 78 with downwardly extending portion 80 which gradually meets outlet 44. It is to be understood that these parameters are illustrative only and no limitation is intended with respect thereto.

It can be seen that a novel blood treatment system has been shown and described which utilizes a venous reservoir that vents the air from the blood in a highly effective manner. The velocity of the blood entering inlet 42 will be sharply decreased as the result of the rapidly expanding volume that it enters in the inlet side of the container 48. As a result of the configuration of container 48, the velocity of the blood flow is kept as low as possible in order to give the blood a long time for bubble release. The velocity of the blood does not increase substantially until the blood is at outlet 44. By spacing the inlet 44 from the vent 46 as far as possible at the inlet end of the container 48, and by providing extending wall 76, bubbles which have not been discharged immediately may flow back up wall 76 to the vent 46.

Since entrance is horizontal into the container and blood will need to manage a 90° turn downward to the outlet, any air bubbles entering the container will slow and natural buoyancy will dominate, forcing the bubbles to the top of the reservoir for venting. The shape of the blood compartment functions as an inhibiting shape to eddies and swirls in the blood which can trap air bubbles and also allows for easy and complete drainage of blood at the end of a surgical procedure.

Although an illustrative embodiment of the invention has been shown and described, it is to be understood that various modifications and substitutions may be made by those skilled in the art without departing from the novel spirit and scope of the present invention.

What is claimed is:

1. A venous reservoir which comprises:
two sheets of flexible material sealed together about the edges to define a bag having a venous blood inlet, a venous blood outlet and a vent outlet, the inlet being located at the lowermost portion of a generally vertical inlet wall of the container to allow the blood entering the inlet to immediately enter a large volume in the bag to cause the blood to expand rapidly, the top of said inlet wall communicating with said vent outlet whereby a sharp decrease in the velocity of the blood flow resulting from its rapid expansion provides buoyancy to air in the blood causing air bubbles to rise to the top of the bag and be vented through said vent opening, said bag having a top wall extending from the vent opening and toward the outlet that is curved in a a manner to prevent the velocity of the blood from increasing until the blood is substantially at the blood outlet, the top wall extending forwardly and downwardly with a curved portion opposite to the inlet whereby the air bubbles that have not been discharged immediately upon entering the reservoir may flow back up the top wall to the vent opening, said inlet wall lying within a plane that is at an angle which approaches ninety degrees with respect to the inlet axis; said inlet being located at the bottom of said inlet wall and the vent opening being located at the top thereof, the vent opening and the blood outlet being diagonally spaced from each other at opposite ends of said container; said inlet being located in a horizontal plane that is higher than the horizontal plane in which the blood outlet is located, the inlet axis being perpendicular to the blood outlet axis and the vent opening axis being parallel to the blood outlet axis.

2. A venous reservoir as described in claim 1, wherein the inlet is located at the bottom of said inlet wall and the vent outlet is located at the top thereof, and wherein the vent outlet and the blood outlet are diagonally spaced from each other.

3. A venous reservoir as described in claim 1, wherein the inlet axis is perpendicular to the outlet axis.

4. A venous reservoir as described in claim 1, wherein the vent outlet axis is parallel to the outlet axis.

* * * * *